US007879877B2

(12) United States Patent
Nagamoto et al.

(10) Patent No.: US 7,879,877 B2
(45) Date of Patent: Feb. 1, 2011

(54) CARBOSTYRIL DERIVATIVES FOR ACCELERATING SALIVATION

(75) Inventors: Hisashi Nagamoto, Tokushima-ken (JP); Masayuki Kohashi, Tokushima (JP); Hiroshi Oka, Yokohama (JP)

(73) Assignees: Otsuka Pharmaceutical Co., Ltd., Tokyo-To (JP); St. Marianna University School of Medicine, Kawasaki-shi (JP)

( * ) Notice: Subject to any disclaimer, the term of this patent is extended or adjusted under 35 U.S.C. 154(b) by 355 days.

(21) Appl. No.: 10/566,214

(22) PCT Filed: Jul. 7, 2004

(86) PCT No.: PCT/JP2004/009992

§ 371 (c)(1), (2), (4) Date: Jan. 27, 2006

(87) PCT Pub. No.: WO2005/011811

PCT Pub. Date: Feb. 10, 2005

(65) Prior Publication Data

US 2007/0112026 A1 May 17, 2007

(30) Foreign Application Priority Data

Jul. 30, 2003 (JP) ............................ 2003-282691
Jan. 29, 2004 (JP) ............................ 2004-021808

(51) Int. Cl.
*A61K 31/47* (2006.01)
*A01N 43/42* (2006.01)

(52) U.S. Cl. ..................................................... 514/312

(58) Field of Classification Search ....................... None
See application file for complete search history.

(56) References Cited

U.S. PATENT DOCUMENTS

| | | | | |
|---|---|---|---|---|
| 4,322,425 A * | 3/1982 | Yabuuchi et al. | ............ | 514/312 |
| 4,578,381 A | 3/1986 | Uchida et al. | | |
| 5,476,858 A * | 12/1995 | Yamasaki et al. | ........... | 514/312 |
| 5,480,891 A | 1/1996 | Yamasaki et al. | | |
| 5,576,331 A | 11/1996 | Yamasaki et al. | | |
| 5,637,597 A | 6/1997 | Matsuda et al. | | |
| 6,060,486 A | 5/2000 | Urashima et al. | | |

FOREIGN PATENT DOCUMENTS

| | | |
|---|---|---|
| EP | 0 543 018 B1 | 5/1993 |
| GB | 2 123 825 A | 2/1984 |
| JP | 3-74329 | 3/1991 |
| JP | 7-101862 | 4/1995 |
| JP | 11-228413 | 8/1999 |
| WO | WO 93/23043 | 11/1993 |
| WO | WO 94/21612 | 9/1994 |
| WO | WO 95/11026 | 4/1995 |
| WO | WO 96/04911 | 2/1996 |
| WO | WO 97/09045 | 3/1997 |
| WO | WO 97/13515 | 4/1997 |
| WO | WO 98/26769 | 6/1998 |

OTHER PUBLICATIONS

Loguercio et al. Effect of Somatostatin on Salivary Secretion in Man. Digestion, 36:91-95, 1987.*

Fox et al. Primary Sjogren syndrome: clinical and immunopathologic features. Semin. Arthritis Rheum. Nov. 14, 1984(2): 77-105.*

Keishi Kawata et al., "Investigation of the Effect of the Rebamipide Mouthwash on the Crisis of the Stomatitis Induced by the Cancel Chemotherapy and/or Radiotherapy," J. New Rem. & Clin. vol. 50, No. 2, 2001, pp. 47-54.

Medical Journal, vol. 37, No. 5, 2001, pp. 1610-1618.

Kazushi Sakurai et al., "Protection by Rebamipide Against Acetic Acid-Induced Colitis in Rates Ralationship with Its Antioxidative Activity," Digestive Diseases and Sciences, vol. 43, No. 9 (Sep. 1998 Supplement), pp. 125S-133S.

"Merck Manual," 1999, Merck, Whitehouse Station, N. J. p. 423, col. 1, para. 5.

* cited by examiner

*Primary Examiner*—Brandon J Fetterolf
*Assistant Examiner*—Anna Pagonakis
(74) *Attorney, Agent, or Firm*—Finnegan, Henderson, Farabow, Garrett & Dunner, L.L.P.

(57) ABSTRACT

Novel pharmaceutical composition for accelerating salivation and for prophylaxis and/or treatment of xerostomia, which comprises as an active ingredient a carbostyril compound of the formula (1), wherein R is a halogen atom, and the substitution position of the subsistuent on said carbostyril nucleus is the 3- or 4-position, and the bond between the 3- or 4-positions of the carbostyril nucleus is either a single bond or a double bond, or a pharmaceutically acceptable salt thereof. The pharmaceutical composition of the present invention exhibits an accelerating activity of salivation, and is useful in the prophylaxis or treatment of Xerostomia or hyposalivation.

(1)

COOH
$CH_2CH$
NHCO
R
N
H
O

4 Claims, No Drawings

CARBOSTYRIL DERIVATIVES FOR ACCELERATING SALIVATION

BACKGROUND OF THE INVENTION

The present invention relates to a pharmaceutical composition for accelerating salivation and use thereof. More particularly, the present invention relates to a pharmaceutical composition for accelerating salivation, which comprises as an active ingredient a carbostyril compound of the formula (1):

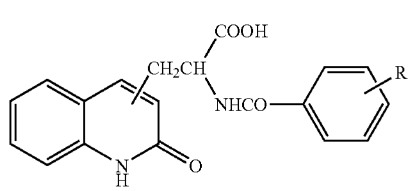

(1)

wherein R is a halogen atom, and the substitution position of the substituent on said carbostyril nucleus is the 3- or 4-position, and the bond between the 3- and 4-positions of the carbostyril nucleus is either a single bond or a double bond, or a pharmaceutically acceptable salt thereof, or preferably comprises as an active ingredient 2-(4-chlorobenzoylamino)-3-(2-quinolon-4-yl)propionic acid or a pharmaceutically acceptable salt thereof, and further relates to a use of said carbostyril compound for salivation and for prophylaxis and/or treatment of xerostomia, as well as a method for accelerating salivation or for prophylaxis and/or treatment xerostomia, which comprises administering orally said carbostyril compound to a subject in need.

BACKGROUND ART

Saliva plays an important role in the maintenance of the oral environments and the oral functions. Namely, there are two functions of saliva of dietary intake function and a function of maintaining the oral environment. With respect to the dietary intake function of saliva, saliva exhibits a digesting action such as formation of alimentary bolus and digestive enzyme action, or an activity of maintaining taste sensation through solubilization of tastant or secretion of gastin (which is a carbonate dehydrogenase). With respect to the function of maintaining oral environments, saliva exhibits self-cleaning effect on the teeth or the mucous membranes, recalcification action of the teeth, antibacterial action, immunization action, tissue repair promoting action by growth factors, etc., and antiinflammatory action.

Recently, there is an increase in the number of the patients, who suffer from hyposalivation caused by various factors. Therefore, the social demand for treatment thereof has been increased. Hyposalivation has been found being accompanied by abnormality of salivary gland per se caused by radiation therapy of parotiditis, as well as by metabolic diseases (e.g., Basedow's disease, diabetes mellitus, etc.), or other diseases such as collagen diseases, and further hyposalivation is caused by stress factors or side effects of various medicines. In the recent aging society, the function of salivary gland is decreased by aging, and various medications for various complicated diseases supervened in the aging people are done, and as a result, it has been considered that a number of patients suffering from hyposalivation would be increased more than ever in future.

In hyposalivation, the tongue is reddened, and sometimes has a crack due to dryness of the oral cavity, by which a patient of hyposalivation complains of a pain when eating, and further complains of difficulty with chewing or swallowing. Further, it is known that hyposalivation causes uncomfortable feeling in the oral cavity, or taste disorders and articulation disorder, and further causes denture unstability, tooth caries, onset of alveolar blennorrhea, mouth inflammation, pneumonia, and digestive dysfunction.

The topical application of artificial saliva is employed as a treatment of hyposalivation, but the effect thereof is temporary and limited. Anethole trithione, which is known as a muscarine receptor agonist, and cevimeline hydrochloride are used as a salivation accelerator, and they have some defects, for example, the effects thereof are unstable and there is a problem of possible side effects in digestive system such as nausea, vomiting, anorexia, abdominal discomfort. Under these circumstances, a new medicament for treatment of hyposalivation has been strongly desired.

The carbostyril compounds of the above formula (1) and a process for preparation thereof are disclosed in JP-B-63-35623, and this literature also discloses that these compounds are useful as an antiulcer agent. It has also been disclosed that the carbostyril compounds are useful in the treatment of various diseases, for example, as an agent for treatment of gastric inflammation (cf., JP-A-3-74329), or as an antidiabetic (cf., JP-A-5-148143). Further, it has also been disclosed that these compounds exhibit a somatostatin increasing activity or an activity of inhibiting somatostatin reduction (cf., JP-A-6-509587). In addition, it has also been disclosed that the present compounds are useful as an agent for protecting intestinal mucosa disorder (cf., JP-A-6-211662), as a urease inhibitor (cf., JA-A-7-101862), and as an interleukin-8 inhibitor (cf., JP-A-8-12578), as a cancer inhibitor (cf., JP-A-9-71532), and as an agent for treatment of eye diseases (cf., JP-A-9-301866). Furthermore, the carbostyril compounds are disclosed to be useful as an inhibitor of ADP-ribosylation (cf., JP-A-10-231246), as an agent for treatment of intravital toxin-type bacterial infection (cf., JP-A-10-231247), and as an NADase inhibitor (cf., JP-A-11-228413).

DISCLOSURE OF INVENTION

As mentioned above, the decrease in salivation function may be a serious problem in view of oral sanitation, and further in order to improve the quality of life of the elderly people, a number of which has been drastically increased, and hence, it has been desired to develop a more effective salivation accelerator, or a more effective agent for prophylaxis or treatment of xerostomia.

The present inventors have been intensively studied in order to find a new medicament for accelerating salivation, and as a result, have found that the carbostyril compounds of the above formula (1), especially 2-(4-chlorobenzoylamino)-3-(2-quinolon-4-yl)propionic acid, or a pharmaceutically acceptable salt thereof exhibits an excellent salivation accelerating activity and also excellent prophylactic and/or therapeutic effects on xerostomia, and finally have accomplished the present invention.

Namely, an object of the present invention is to provide a pharmaceutical composition for accelerating salivation comprising as an active ingredient a carbostyril compound of the above formula (1) or a pharmaceutically acceptable salt thereof in admixture with a conventional pharmaceutically acceptable diluent or carrier, which is especially useful in the prophylaxis or treatment of a patient suffering from hyposalivation. The present invention further provides a pharmaceutical composition for prophylaxis and/or treatment of xerostomia, which comprises as an active ingredient a carbostyril compound of the above formula (1) or a pharmaceutically acceptable salt thereof in admixture with a conventional pharmaceutically acceptable diluent or carrier. Furthermore, the present invention provides use of the carbostyril compound of the formula (1) for manufacturing a medicament useful for accelerating salivation and for prophylaxis and/or treatment of xerostomia and further provides a method for accelerating salivation and for prophylaxis and/or treatment of xerostomia by administering the carbostyril compound of the formula (1) to a subject in need.

The present invention includes the following embodiments.

1. A pharmaceutical composition for accelerating salivation for oral administration, which comprises as an active ingredient a carbostyril compound of the formula (1) or a pharmaceutically acceptable salt thereof in admixture with a conventional pharmaceutically acceptable diluent or carrier.

2. The pharmaceutical composition for accelerating salivation for oral administration according to the above 1, wherein the active ingredient is 2-(4-chlorobenzoylamino)-3-(2-quinolon-4-yl)propionic acid or a pharmaceutically acceptable salt thereof.

3. The pharmaceutical composition for accelerating salivation for oral administration according to the above 1 or 2, which is a medicament for prophylaxis or treatment of xerostomia.

4. The pharmaceutical composition for accelerating salivation for oral administration according to the above 1 or 2, which is a medicament for prophylaxis and/or treatment of xerostomia accompanying Sjögren's syndrome or of hyposalivation.

5. A pharmaceutical composition for prophylaxis and/or treatment of xerostomia for oral administration, which comprises as an active ingredient a carbostyril compound of the formula (1) or a pharmaceutically acceptable salt thereof in admixture with a conventional pharmaceutically acceptable diluent or carrier.

6. The pharmaceutical composition for prophylaxis and/or treatment of xerostomia for oral administration, according to the above 5, wherein the xerostomia is xerostomia accompanying Sjögren's syndrome.

7. The pharmaceutical composition for prophylaxis and/or treatment of xerostomia for oral administration according to the above 5 or 6, wherein the active ingredient is 2-(4-chlorobenzoylamino)-3-(2-quinolon-4-yl)propionic acid or a pharmaceutically acceptable salt thereof.

8. Use of a carbostyril compound of the formula (1) for manufacturing a medicament useful for accelerating salivation and for prophylaxis and/or treatment of xerostomia.

9. Use according to the above 8, wherein the active ingredient is 2-(4-chlorobenzoylamino)-3-(2-quinolon-4-yl)propionic acid or a pharmaceutically acceptable salt thereof.

10. A method for accelerating salivation which comprises administering orally a carbostyril compound of the formula (1) to a subject in need.

11. A method for prophylaxis and/or treatment of xerostomia, which comprises administering orally the carbostyril compound of the formula (1) to a subject in need.

12. The method according to the above 10 or 11, wherein the active ingredient is 2-(4-chlorobenzoylamino)-3-(2-quinolon-4-yl)propionic acid or a pharmaceutically acceptable salt thereof.

DETAILED DESCRIPTION OF THE INVENTION

The pharmaceutical composition for accelerating salivation or for prophylaxis and/or treatment of xerostomia of the present invention comprises as an active ingredient the carbostyril compound of the above formula (1) or a pharmaceutically acceptable salt thereof, and may be formulated into a conventional pharmaceutical preparation.

The pharmaceutical preparation is formulated by using conventional pharmaceutically acceptable diluents or carriers such as fillers, thickening agents, binders, wetting agents, disintegrators, surfactants, lubricants, and the like. The pharmaceutical preparations can be selected from various forms in accordance with the desired utilities, and the representative forms are tablets, pills, powders, solutions, suspensions, emulsions, granules, capsules, syrups, and the like. In addition, the present pharmaceutical composition can be prepared in admixture with a resin so that the sustained-release property can be increased. The pharmaceutical composition for accelerating salivation or for prophylaxis and/or treatment of xerostomia of the present invention is preferably prepared in the form of a pharmaceutical composition for systemic administration, particularly in the form of a pharmaceutical composition for oral administration such as tablets, pills, powders, solutions, suspensions, emulsions, granules, syrups, and capsules, and the like.

In order to form in tablets, there are used well known pharmaceutically acceptable carriers such as vehicles (e.g., lactose, white sugar, sodium chloride, glucose, urea, starch, xylitol, mannitol, erythritol, sorbitol, calcium carbonate, kaolin, crystalline cellulose, silicic acid, etc.), binders (e.g., water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g., dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g., white sugar, stearin, cacao butter, hydrogenated oils, etc.), absorption promoters (e.g., quaternary ammonium base, sodium laurylsulfate, etc.), wetting agents (e.g., glycerin, starches, etc.), adsorbents (e.g., starches, lactose, kaolin, bentonite, colloidal silicates, etc.), lubricants (e.g., purified talc, stearates, boric acid powder, polyethylene glycol, etc.), and the like. Moreover, the tablets may also be in the form of a conventional coated tablet, such as sugar-coated tablets, gelatin-coated tablets, enteric coating tablets, film coating tablets, or double or multiple layer tablets.

In the preparation of pills, the conventional pharmaceutically acceptable carriers can be used and include, for example, vehicles (e.g., glucose, lactose, starches, cacao butter, hydrogenated vegetable oils, kaolin, talc, etc.), binders (e.g., gum arabic powder, tragacanth powder, gelatin, ethanol, etc.), disintegrators (e.g., laminaran, agar, etc.) and the like. Capsules can be prepared by charging a mixture of the active ingredient and the above carriers into hard gelatin capsules, soft capsules or hydroxypropylmethyl cellulose capsules (HPMC capsules) in usual manner.

The amount of the carbostyril compound (1) or a pharmaceutically acceptable salt thereof to be incorporated into the pharmaceutical composition of the present invention is not specified but may be selected from a broad range, but usually, it is preferably in the range of about 0.001 to 70% by weight, more preferably in the range of about 0.005 to 50% by weight, based on the whole weight of the composition. In the particularly preferable oral composition for accelerating salivation or for prophylaxis and/or treatment of xerostomia, the amount of the active compound (1) or a pharmaceutically acceptable salt thereof is preferably in the range of about 0.005 to 5% by weight, more preferably in the range of 0.01 to 3 % by weight, based on the whole weight of the composition.

The suitable method for administration of the present composition may be determined in accordance with various forms of preparations, ages, sexes and other conditions of the patients, the degree of severity of diseases, and the like. For example, tablets, pills, solutions, suspensions, emulsions, granules, syrups and capsules are administered orally.

The dosage of the medicament of the present invention may be selected in accordance with the usage, ages, sexes and other conditions of the patients, the degree of severity of the diseases, and the like, but the amount of the carbostyril compound (1) or a pharmaceutically acceptable salt thereof is usually in the range of 0.01 to 50 mg/kg of body weight per day. In addition, the active ingredient may be contained in the range of 1 to 1000 mg per single dosage unit.

EFFECTS OF INVENTION

The pharmaceutical composition for accelerating salivation or for prophylaxis and/or treatment of xerostomia of the present invention can promote the saliva secretion and/or can exhibit prophylactic and/or therapeutic effects on xerostomia by administering to a patient of hyposalivation, so that the present pharmaceutical composition can be useful as a medicament for prophylaxis or treatment of dry mouth or xerostomia or hyposalivation, which may cause various oral diseases such as burning sensation of the mouth, taste disorder, glossalgia, periodontal diseases, and the like.

The pharmaceutical composition for accelerating salivation or for prophylaxis and/or treatment of xerostomia of the present invention is very weak in an activity mediated by a muscarine M3 receptor (CHRM3), and hence, when the composition is administered orally, it exhibits more potent effects for acceleration of salivation or for prophylaxis and/or treatment of xerostomia in comparison with the effects for promoting secretion in lacrimal gland. Furthermore, the composition of the present invention has less side effects, particularly less side effects on the digestive tract such as nausea, vomiting, anorexia, abdominal discomfort and hence can be used with high safety.

BEST MODE FOR CARRYING OUT THE INVENTION

The pharmaceutical composition for accelerating salivation or for prophylaxis and/or treatment of xerostomia of the present invention, which is suitable for oral administration, may be prepared and used in various forms as mentioned above, and the present invention is illustrated by the following Preparations and Pharmacological Experiments, but should not be construed to be limited thereto.

| Preparation 1 | |
|---|---|
| 2-(4-Chlorobenzoylamino)-3-(2-quinolon-4-yl)propionic acid | 150 g |
| Avicel (Trade Mark, manufactured by Asahi Kasei Corporation) | 40 g |
| Corn Starch | 30 g |
| Magnesium stearate | 2 g |
| Hydroxypropyl methylcellulose | 10 g |
| Polyethylene glycol-6000 | 3 g |
| Castor Oil | 40 g |
| Methanol | 40 g |

The active compound of the present invention, Avicel, corn starch and magnesium stearate are mixed and kneaded and the mixture is tabletted by using a conventional pounder (R 10 mm) for sugar coating. The tablets thus obtained are coated with a film coating agent consisting of hydroxypropyl methylcellulose, polyethylene glycol-6000, castor oil and ethanol to give film coating tablets.

| Preparation 2 | |
|---|---|
| 2-(4-Chlorobenzoylamino)-3-(2-quinolon-4-yl)propionic acid | 150 g |
| Citric acid | 1.0 g |
| Lactose | 33.5 g |
| Dicalcium phosphate | 70.0 g |
| Pullonic F-68 | 30.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium laurylsulfate | 3.0 g |
| Dry magnesium stearate | 3.0 g |
| Ethanol | q.s. |

The active compound of the present invention, citric acid, lactose, dicalcium phosphate, Pullonic F-68 and sodium laurylsulfate are mixed. The mixture is screened with No. 60 screen and is granulated with an alcohol solution containing polyvinylpyrrolidone, Carbowax 1500 and Carbowax 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape. The core tablets thus prepared are varnished and dusted with talc in order to guard them from wetting. Undercoating is applied to the core tablets. In order to administer the tablets orally, the core tablets are varnished several times. In order to give round shape and smooth surface to the tablets, further undercoating and coating with a lubricant are applied thereto. The tablets are further coated with a coloring coating materials until the desired colored tablets are obtained. After drying, the coated tablets are polished to obtain the desired tablets having uniform gross.

EXPERIMENT 1

The effects of the present active compound on salivation in anesthetized rats were studied as mentioned below.

Method of Experiment

1) Preparation of experimental models:

Models for studying salivation were prepared according to the method of Masunaga, et al. (Masunaga, H., et al., Long-lasting salivation induced by a novel Muscarinic receptor agonist SNI-201 in rats and dogs. Eur. J. Pharmacol., 339: 1-9, 1997).

Namely, rats had been fasted from the day before the experiment except that the intake of water was freely allowed, and the rats were anesthetized with Nembutal (=pentobarbital sodium). The rats were put down on the back, and the neck was subjected to midline incision. An ATOM anionic fluid suction catheter of 6Fr. was inserted to the air tube in order to keep the airway clear. Next, a polyethylene tube (SP55 Natsume) containing a solution of 10 U/ml heparin in physiological saline was inserted into the carotid artery for administration of a medicament.

2) Measurement of the salivation amount:

A 0.03 mg/ml or 0.1 mg/ml solution of the test compound (2-(4-Chlorobenzoylamino)-3-(2-quinolon-4-yl)-propionic acid; general name: Rebamipide) in 2% aqueous sodium hydrogen carbonate solution, and a vehicle (2% aqueous sodium hydrogen carbonate solution) as a control solution were used, and the test compound solution and the control solution in an amount of 1 mL/kg were respectively administered intravenously via the polyethylene tube inserted into the carotid artery. Then, the salivation amount was measured every 10 minutes for 20 minutes with using cotton swabs, and the salivation amount per one minute was calculated from the total salivation amount for this period.

In this measurement, the salivation amount was measured in such a way that the dried cotton swab (the weight thereof was previously measured) was inserted into the mouth of rat, and the swab was exchanged with a new dried one in every ten minutes, and the total salivation amount was calculated from the difference in the weight of the swab between before and after inserting into the mouth.

Results:

The average salivation amount was calculated as measured in the vehicle-treated group (5 animals), the test compound (0.03 mg/kg)-treated group (5 animals) and the test compound (0.1 mg/kg)-treated group (4 animals), and the percentage of the average salivation amount in the test compound-treated groups against that of the vehicle-treated group was calculated. The results are shown in Table 1.

As shown in Table 1, the average ± standard error of the salivation amount in the vehicle-treated group was 0.128±0.008 mg/min (n=5), while those of the test compound (0.03 mg/kg)-treated group and the test compound (0.1 mg/kg)-treated groups were 0.262±0.084 mg/min (n=5) and 0.305±0.097 mg/min (n=4), respectively. Thus, by intravenously administering a test compound in an amount of 0.03 or 0.1 mg/kg, it was observed that the salivation amount was increased by 205% and 239%, respectively in comparison with the vehicle-treated control group.

TABLE 1

| | Salivation amount | |
|---|---|---|
| | (mg/min) | (%) |
| Vehicle-treated Group (n = 5) | 0.128 ± 0.008 | 100 |
| Test compound (0.03 mg/kg) - treated Group (n = 5) | 0.262 ± 0.084 | 205 |
| Test compound (0.1 mg/kg) - treated Group (n = 4) | 0.305 ± 0.097 | 239 |

The salivation amount is expressed by the average ± standard error, and the comparison with the vehicle-treated group is expressed by %.

Conclusion:

As is apparent from the above results, the salivation amount was dose-dependently increased by intravenous administration of a test compound in anesthetized rats. Thus, it was proved that the test compound exhibits an activity of accelerating salivation by systemic administration.

EXPERIMENT 2

The effects of the present active compound by intragastric administration in non-anesthetized rats with respect to the salivation were studied as mentioned below.

Method of Experiment

Using non-anesthetized rats, the saliva being swallowed for 4 hours on awaking into the diverticulum placed at the esophagus was collected and the salivation amount (g) was measured.

Vehicle (0.5% sodium carboxymethyl cellulose solution) or Rebamipide 10, 30 or 100 mg/kg was intragastrically administered once when the esophagus diverticulum was set, and as a result, the average ± standard error of the salivation amount was 0.88±0.23 g (n=7) in the vehicle-treated group, 0.99±0.21 g (n=8) in the Rebamipide (10 mg/kg)-treated group, 1.37±0.26 g (n=7) in the Rebamipide (30 mg/kg)-treated group, and 1.72±0.40 g (n=8) in the Rebamipide (100 mg/kg)-treated group.

Conclusion:

As is apparent from the above results, the salivation amount was dose-dependently increased by intragastrical administration of Rebamipide in non-anesthetized rats. Thus, it was proved that the active compound of the present invention exhibits an accelerating activity of salivation by intragastrical administration.

EXPERIMENT 3

The effects of the present active compound on xerostomia in patients with Sjögren's syndrome was tested.

(1) Subjects to be Tested:

The test was carried out for 21 patients (age: 27 to 85 years old, all female) who were diagnosed as surely having Sjögren's syndrome on the basis of Revised Diagnosis Standard for Sjögren's syndrome (issued by Ministry of Health, Labour and Welfare in Japan in 1999).

(2) Administration method:

Tablet containing 2-(4-chlorobenzoylamino)-3-(2-quinolon-4-yl)propionic acid (100 mg per tablet) was orally administered three times per day immediately after a meal (one tablet for each time) for 8 weeks.

(3) Evaluation method:

i) Evaluation by patients themselves as to subjective symptoms (e.g. feeling of dryness of the mouth, hydromania, pain in the mouth, taste disorder, difficulty in dietary intake, abnormality of saliva) before administration of tablet, after administration of tablet for 4 weeks and 8 weeks, respectively. Based on the total scores at the time of studying, the changing rate was calculated by the following equation:

$$\text{Improved rate of subjective symptoms (\%)} = \frac{\left(\begin{array}{c}\text{Total score before administration}- \\ \text{Total score after administration}\end{array}\right)}{\text{Total score before administration}} \times 100$$

wherein the improvement of subjective symptoms were scored in the following four degrees:

0: No improvement

1: Lightly improved

2: Moderately improved

3: Highly improved ii) Besides, the salivation amount (volume of secreted saliva) was measured by Saxon Test before administration of tablet, after administration of tablet for 4 weeks and 8 weeks, respectively. Based on the salivation amount thus measured, the increasing rate of salivation was determined by the following equation:

$$\text{Increasing rate of salivation (\%)} = \frac{\left(\begin{array}{c}\text{Volume of saliva before administration}-\\ \text{Volume of saliva after administration}\end{array}\right)}{\text{Volume of saliva before administration}} \times 100$$

The effects of the test compound were evaluated based on both of the improvement of subjective symptoms and the salivation amount, which was classified in three degrees as follows.

"Remarkably effective": Both of the improved rate of subjective symptoms and the increasing rate of salivation being more than 50%;

"Effective": Either of the improved rate of subjective symptoms or the increasing rate of salivation being more than 50%;

"Non-effective": Neither the improvement of subjective symptoms nor the increasing of salivation being observed.

The experimental results were statistically evaluated in accordance with Wilcoxon's rank test.

(4) Results:

Total scores of subjective symptoms were 9.6±4.1 before administration of tablet, 6.6±3.2 after administration of tablet for 4 weeks, and 5.2±2.6 after administration of tablet for 8 weeks. Thus, the subjective symptoms was significantly improved by the administration of the present active compound.

Besides, the salivation amount was 1.29±1.00 g before administration of tablet, but it was 1.95±1.21 g after administration of tablet for 4 weeks, and 1.93±1.14 g after administration of tablet for 8 weeks, and hence, the salivation amount was also significantly increased by administration of the present active compound.

Overall evaluation were as follow:

(i) After administration of tablet for 4 weeks:

"Remarkably effective": 2 patients

"Effective": 9 patients

"Non-effective": 10 patients (ii) After administration of tablet for 8 weeks:

"Remarkably effective": 6 patients

"Effective": 7 patients

"Non-effective": 8 patients

The effectiveness was 52.4% after administration of tablet for 4 weeks and 61.9% after administation of tablet for 8 weeks.

EXPERIMENT 4

Effects of the present compound 2-(4-chlorobenzoylamino-3-(2-quinolon-4-yl)propionic acid on a patient suffering from mouth dryness accompanying Sjögren's syndrome:

(1) Patient: A female, 27 years old.

(2) Chief complaint: cotton mouth, mattering of eyes.

(3) Patient record:

Around Feb. 1999, the patient visited a hospital in view of dryness of mouth and difficulty in tearing. Then, she was diagnosed to have Sjögren's syndrome in view of antinuclear antibody: 160 times, anti-SSR-A antibody: 126 times, Gum test: 8 ml, lowered function of salivary gland, ophthalmic Silmer test (right 4 mm, left 3 mm), dry kerato-conjunctivitis. Sebimerine hydrochloride was administered but the administration was stopped because of side effects of such as abdominal discomfort and stomach ache. Besides, Salivate spray was also applied but it was not effective and discontinued. After moving her home because of marriage, her hospital was change on May. 1, 2003. Before the changing the hospital, an ophthalmic drop containing chondroitin sulfate has frequently been used for treating dry conjunctivitis.

(4) Symptoms and examination findings when tested in the new hospital:

The symptoms of the mouth dryness were significant dry of toungue and significant lowering of salivaition (0.52 g in Saxon test). No swelling of parotid gland. Eye dryness was Silmer test (right 2 mm, left 1 mm), Rose bengal test (3+). No inflammation of the eye. Examination findings were ESR 17 mm/hr., WBC 5500/μL, RBC 484×$10^4$/μL, Hgb 13.4 g/dL, T.P. 8.4 g/dL, Alb 4.4 g/dL, AST 17 IU/mL, ALT 9 IU/mL, Amylase 140 IU/L, CK 46 IU/L, Cr 0.69 mg/dL, BUN 14.0 mg/dL, CRP<0.3 mg/dL, ANA 640 folds (speckled pattern), anti-SS-A antibody 126 times, Anti-SS-B antibody, negative, IgG 2270 mg/dL, IgA 368 mg/dL, IgM 132 mg/dL, and immune complex, Ciq solid-phase method, 3.3 (positive).

(5) Clinical course:

The amount of saliva was 0.52 g in Saxon test on May 1, 2003 and 0.89 g on May. 29, 2003, and the patient showed significant mouth dryness. Administration of 2-(4-chlorobenzoylamino)-3-(2-quinolon-4-yl)propionic acid (300 mg/day)was started on May. 29, 2003. The salivation amount significantly increased to 1.55 g on Jun. 25, 2003 and then the subjective symptoms were improved. The salivation amount more increased to 1.86 g on Jul. 23, 2003 and then the subjective symptoms were also more improved.

INDUSTRIALLY APPLICABILITY

The pharmaceutical composition for accelerating salivation and for prophylaxis and/or treatment of xerostomia of the present invention is useful in the prophylaxis and/or treatment of patients suffering from hyposalivation, for example, patients showing symptoms or general symptoms such as dry mouth caused by viscous feeling of saliva or viscosity promotion, etc., or oral burning; taste disorder; difficulty of food intake such as swallowing dysfunction; glossalgia or pain of the oral mucous membrane such as erythema of the tongues atrophy of tongue papilla, smooth tongue, etc.; fragile of the oral mucous membrane; disorders caused by reduction of self-cleaning function such as angulus infectiosus, candida, tooth caries, highly onset of tooth caries, periodontal disease, oral mucosa diseases, ill-fitting denture, denture ulcer.

Especially, hyposalivation has many symptoms such as dehydration, elevated temperature or mouth respiration caused by stress, drying, fever or severe vomiting or diarrhea, or hyposalivation may onset in the middle of the treatments, for example, caused by side effects of a medicine, radiation therapy, or surgical excision of salivary gland. Further, the present pharmaceutical composition is useful in the prophylaxis and/or treatment of xerostomia or hyposalivation accompanying Sjögren's syndrome, rheumatoid arthritis, hidebound disease, multiple myositis, systemic lupus erythematosus, diabetes mellitus, kidney failure, diabetes insipidus, nerve injury, loss of mastication function, senile atrophy of salivary gland.

The invention claimed is:

1. A method for accelerating salivation which comprises administering orally the carbostyril compound of 2-(4-chlorobenzoylamino)-3-(2-quinolon-4-yl)propionic acid or a pharmaceutically acceptable salt thereof to a subject in need and detecting accelerated salivation in the subject.

2. A method for treatment of xerostomia which comprises administering orally the carbostyril compound of 2-(4-chlorobenzoylamino)-3-(2-quinolon-4-yl)propionic acid or a pharmaceutically acceptable salt thereof to a subject in need and detecting accelerated salivation in the subject.

3. The method according to claim 1, which is a method for treatment of xerostomia accompanying Sjögren's syndrome or of hyposalivation.

4. The method according to claim 2, wherein the xerostomia is xerostomia accompanying Sjögren's syndrome.

* * * * *